United States Patent
Carpenter et al.

(10) Patent No.: US 10,022,409 B2
(45) Date of Patent: *Jul. 17, 2018

(54) COMPOSITIONS AND METHODS FOR IMPROVING HUMAN HEALTH AND NUTRITION

(71) Applicant: BIOWISH TECHNOLOGIES, INC., Cincinnati, OH (US)

(72) Inventors: Richard S. Carpenter, West Chester, OH (US); E. Wesley Huff, Pleasant Grove, UT (US); Amit Kapur, East Corrimal (AU)

(73) Assignee: BiOWiSH Technologies, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,675

(22) Filed: Jul. 11, 2017

(65) Prior Publication Data
US 2017/0304377 A1    Oct. 26, 2017

Related U.S. Application Data

(63) Continuation of application No. 14/710,434, filed on May 12, 2015, now Pat. No. 9,717,767.

(60) Provisional application No. 61/992,055, filed on May 12, 2014.

(51) Int. Cl.
| | |
|---|---|
| *A61K 35/747* | (2015.01) |
| *A61K 35/742* | (2015.01) |
| *A61K 9/16* | (2006.01) |
| *A23L 33/135* | (2016.01) |
| *A61K 35/745* | (2015.01) |
| *A61K 9/00* | (2006.01) |
| *A23L 33/21* | (2016.01) |
| *A61K 35/00* | (2006.01) |

(52) U.S. Cl.
CPC .......... *A61K 35/747* (2013.01); *A23L 33/135* (2016.08); *A23L 33/21* (2016.08); *A61K 9/0014* (2013.01); *A61K 9/16* (2013.01); *A61K 35/742* (2013.01); *A61K 35/745* (2013.01); *A61K 2035/115* (2013.01)

(58) Field of Classification Search
CPC ...... A23L 33/135; A23L 33/21; A23L 1/3014; A23L 1/308; A61K 2035/115; A61K 35/742; A61K 35/745; A61K 35/747; A61K 9/0014; A61K 9/16; A23V 2002/00; A23V 2200/3202; A23V 2200/3204
See application file for complete search history.

(56) References Cited

U.S. PATENT DOCUMENTS

| | | | |
|---|---|---|---|
| 2004/0086491 A2* | 5/2004 | Monte | A61K 35/745 424/93.4 |
| 2006/0165661 A1* | 7/2006 | Speelmans | A23C 9/16 424/93.4 |
| 2007/0269515 A1 | 11/2007 | Henriksen | |
| 2009/0169531 A1* | 7/2009 | Lacoste | A23C 9/1234 424/93.45 |
| 2009/0274662 A1 | 11/2009 | Magowan | |
| 2010/0074994 A1 | 3/2010 | Harel | |

FOREIGN PATENT DOCUMENTS

| | | |
|---|---|---|
| CN | 101294142 A | 10/2008 |
| CN | 101612169 A | 12/2009 |
| CN | 102599348 A | 7/2012 |
| WO | WO 2014/183117 A1 | 11/2014 |

OTHER PUBLICATIONS

Kiessling G. et al., "Long-term consumption of fermented dairy products over 6 months increases HDL cholesterol", *European Journal of Clinical Nutrition*, vol. 56, No. 9, Sep. 1, 2002 (Sep. 1, 2002), pp. 843-849.

Takemura N. et al., "Inulin Prolongs Survival of Intragastrically Administered Lactobacillus plantarum No. 14 in the Gut of Mice Fed a High-Fat Diet", *The Journal of Nutrition*, vol. 140, No. 11, Sep. 2010 (Sep. 8, 2010), pp. 1963-1969.

Choe D.W. et al., "Egg production, faecal pH and microbial population, small intestine morphology, and plasma and yolk cholesterol in laying hens given liquid metabolites produced by *Lactobacillus plantarum* strains", *British Poultry Science*, vol. 53, No. 1, Feb. 1, 2012 (Feb. 1, 2012), pp. 106-115.

Sanz Y. et al., "Gut microbiota in obesity and metabolic disorders", *Proceedings of the Nutrition Society*, vol. 69, No. 3, Jun. 14, 2010 (Jun. 14, 2010), pp. 434-441.

Tsilingiri K. et al., "Postbiotics: what else?", *Beneficial Microbes*, vol. 4, No. 1, Mar. 1, 2013 (Mar. 1, 2013), pp. 101-107.

International Search Report and Written Opinion issued for PCT/US2015/030374 and dated Aug. 4, 2015.

Nuraida, Food Science and Human Wellness 2015, vol. 4, pp. 47-55.

Wu Mangang et al. "Proliferation culture of Lactobacillus plantarum and preparation of its Concentrated freeze-dried leavening agent" *Food and Fermentation Industry*, vol. 40, No. 1, 2014, 21 pages (machine translation included).

* cited by examiner

*Primary Examiner* — Mark V Stevens

(74) *Attorney, Agent, or Firm* — Cooley LLP; Ivor R. Elrifi; Cynthia Kozakiewicz

(57) ABSTRACT

The present invention provides compositions and methods of promoting human health and nutrition.

15 Claims, 16 Drawing Sheets

Subject

COMPOSITIONS AND METHODS FOR IMPROVING HUMAN HEALTH AND NUTRITION

RELATED APPLICATIONS

This application is a continuation of U.S. patent application Ser. No. 14/710,434, filed May 12, 2015, now allowed, which claims priority to and benefit of U.S. Provisional Application No. 61/992,055 filed on May 12, 2014 the contents of which is hereby incorporated by reference in its entirety.

FIELD OF THE INVENTION

The present invention relates to compositions containing a mixture of pre-, pro- and post-biotic materials and their use in promoting human health and nutrition.

BACKGROUND OF THE INVENTION

Pre-, Pro-, and post-biotics are relatively new terms used to describe a range of materials that have demonstrated benefits in human health. Typically, the term prebiotic refers to a material that stimulates the growth and/or activity of bacteria in the digestive system resulting in beneficial health effects. Prebiotics may be selectively fermented or non-fermented ingredients that allow specific changes, both in the composition and/or activity of the gastrointestinal microflora, which confer health benefits upon the host. Probiotics generally refer to microorganisms that contribute to intestinal microbial balance which in turn play a role in maintaining health. Many species of lactic acid bacteria (LAB) such as, *Lactobacillus* and *Bifidobacterium* are generally considered as Probiotics, but some species of *Bacillus*, and some yeasts have also been found as suitable candidates. Postbiotics refer to non-viable bacterial products or metabolic by products from probiotic organisms that have biologic activity in the host.

The use of Probiotics to improve human and/or animal health is well documented in the literature. In addition, prebiotics and postbiotics offer potential alternatives or adjunctive therapies to the use of live microorganisms and their metabolites. The mechanisms by which these materials beneficially affect human/animal health are typically divided into one of two general categories. The first, modulation of the immune response, and second, antagonism of pathogens either by the production of antimicrobial compounds or through competition for mucosal binding sites. This leads to a suppression of pathogen growth or epithelial binding and hence reduces invasion by pathogenic bacteria and improves the bioavailability and absorption of nutrients, and acts as nutritional intervention in human health.

There is an increasing appreciation of the impact of pre-, pro-, and postbiotics on the modulation of the immune response, more specifically their role in modulating the expression of cytokines that regulate inflammatory responses which can be measured at a local and systemic level. The ingestion of probiotic bacteria, for example, can potentially stabilize the immunologic barrier in the gut mucosa by reducing the generation of local pro-inflammatory cytokines. Alteration of the properties of the indigenous microflora by probiotic therapy has been shown to reverse some immunologic disturbances in acute syndromes such as dysbiosis, one of the most common disorders of the digestive system, and mitigate some chronic conditions characteristic of Crohn's disease, food allergy, and atopic eczema.

Several probiotic species or their postbiotic products induce protective cytokines, including IL-10 and TGF-beta, and suppress pro-inflammatory cytokines, such as TNF, in the mucosa of healthy patients, patients with inflammatory bowel disease and mouse models. Although there is suggestive evidence for each of these claims, the molecular details behind these mechanisms remains almost entirely undetermined.

Primary clinical interest in the application of probiotics has been in the prevention and treatment of infectious diseases including bacterial and viral associated diarrhea. The use of probiotics for control of chronic inflammatory diseases such as pouchitis and ulcerative colitis has also received considerable attention. Moreover, the consumption of pre-, pro- and postbiotics has been linked to the improvement of a wide variety of health conditions, including high cholesterol, rheumatoid arthritis and lactose intolerance.

Despite the growing literature on the benefits of various "biotic" therapies, the beneficial effects of combined pre-, pro-, and postbiotic therapies is less well documented. There remains need for therapeutic compositions combining these therapies to provide a range of health benefits.

SUMMARY OF THE INVENTION

In one aspect the invention provides compositions containing a mixture of a prebiotic, a probiotic comprising a mixture of *Lactobacillus* and/or *Bifidobacterium* microorganisms produced by solid substrate and submerged liquid fermentation and a postbiotic derived from the liquid fermentation medium of the *Lactobacillus* and/or *Bifidobacterium* microorganism, hereinafter referred to as Microbiotic Composites™.

The prebiotic is for example, inulin, fructo-oligosaccharides, and gluco-oligosaccharides. The *Lactobacillus* microorganisms include for example *Pediococcus acidilactici, Pediococcus pentosaceus, Lactobacillus plantarum*. The *bifidobacterium* is for example, *bifidobacterium animalis*.

In some embodiments a mixture of *Lactobacillus* microorganisms is prepared by combining a solid substrate fermentation of *Pediococcus acidilactici, Pediococcus pentosaceus*, and *Lactobacillus plantarum*; and a mixture of bacteria including *Pediococcus acidilactici, Pediococcus pentosaceus*, and *Lactobacillus plantarum* produced by submerged liquid fermentation. Each of the bacteria in the mixture are individually anaerobically fermented, harvested, dried, and ground to produce a powder having a mean particle size of 295 microns, with 60% of the mixture in the size range between 175-900 microns.

In some aspects the *Lactobacillus* from the solid substrate and liquid fermentations are mixed in equal proportion by weight.

The postbiotic is prepared, for example, by collecting the supernatants from the centrifugation of each of the individual anaerobic fermentations of *Pediococcus acidilactici, Pediococcus pentosaceus, Lactobacillus plantarum* and optionally *bifidobacterium animalis*; mixing the supernatants together; freeze-drying the mixed supernatants to a moisture content less than about 5% by weight; grinding the dried supernatants of step (c) to a mean particle size of 295 microns, with 60% of the mixture in the size range between 175-900 microns.

In various embodiments the Microbiotic Composites™ of prebiotic, probiotic, and postbiotic components are combined in equal weight proportion and/or in preferred blend ratios of the three components Also included in the invention are Microbiotic Composites™ containing compositions according to the invention, and a vitamin, a mineral, a sugar, a botanical, or a fungal component. The vitamin is for example, Vitamin A, Vitamin B1, B2, B3, B5, B6, B7, B9, B12, Vitamin C, Vitamin D, Vitamin E or Vitamin K. The mineral is for example, Calcium Carbonate, Calcium Lactate, Calcium Chloride, Calcium Phosphate (dibasic), Sodium Chloride, Potassium Citrate monohydrate, Potassium sulfate, Potassium Phosphate monobasic, Magnesium Oxide, Manganese Carbonate, manganese glucanate, Ferric Citrate, Zinc Carbonate, Zinc glucanate, Cupric Carbonate, Potassium Iodate, Sodium Selenite pentahydrate, Chromium potassium sulfate dodecahydrate, Ammonium paramolybdate tetrahydrate, Sodium meta-silicate nonahydrate, Lithium chloride, boric acid, sodium fluoride, Nickel Carbonate hydroxide tetrahydrate, or ammonium meta-vanadate.

The sugar is for example, dextrose, sucrose, fructose, inulin, trehalose or salts of gluconic acid.

The botanical is for example, *Rhodiola Rosea* extract, *Aloe Barbedensis, Yucca Schidigera, Aloe vera, Boswellia* extract, *Acacia Catechu, Scutellaria baicalensis, moringa* or turmeric The fungal component is for example, *Gandoderma lucidium, Lentinus edodes, Hericium erinaceous, Agaricus blazei, Cordyceps sinensis, Grifola frondosa, Coriolus veriscolor, Coprinus comatus,* or *Grifola frondosa*.

In a further aspect the invention provides methods of improving human health by administering to the subject the composition according to the invention. Preferably, the compositions are administered orally by a tablet, capsule, powder, or granulate. Each tablet, capsule, powder, or granulate contains between about 5-800 milligrams. Optionally, the compositions of the invention are formulated into a skin cream, lotion, liquid, dispersion, gel or ointment such as to administer topically. Additionally, the composition is formulated into a liquid, cream, lotion, dispersion, gel or ointment.

In some aspects the composition is present at between 0.1-10% by weight, preferably between 1-5% by weight.

Also included in the invention are methods of treating dysbiosis, constipation and chronic diarrhea by orally administering the compositions the invention.

Further included in the invention are methods of reducing comorbidities associated with Metabolic Syndrome X by orally administering the compositions the invention.

Additionally, the invention provides methods for treating Rosacea, Acne, Eczema, Dermatitis or Psoriasis comprising topically administering the compositions of the invention via creams, lotions, gels, ointments and/or sprays.

In yet a further aspect the invention provides methods for improving wound healing comprising administering to the wound the compositions the invention.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

Figure 1:
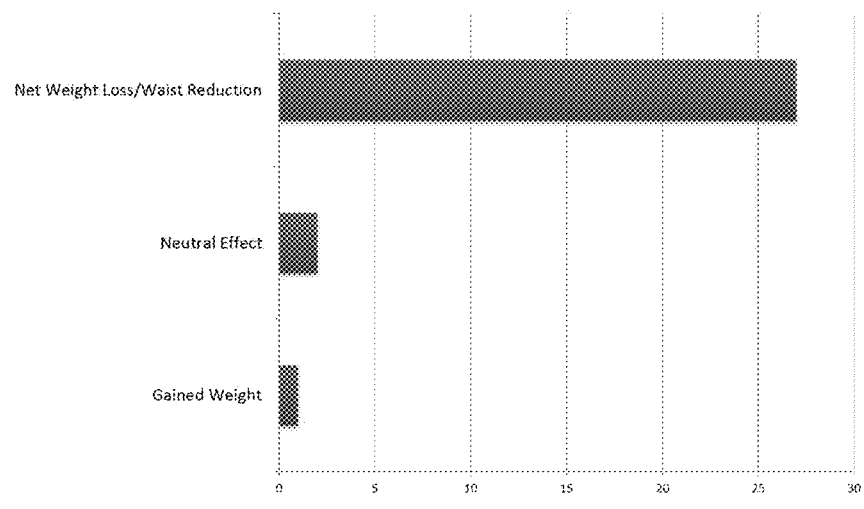
FIG. 1: Weight changes in test subjects following 12 week ingestion of Microbiotic Composite Example 2E

The invention provides a composition consisting of a mixture of specific Microbiotic Composites™ (pre-, pro- and postbiotics) that are useful in promoting overall human health, when given as orally as a nutritional intervention. For example, the compositions of the invention are useful in promoting digestive heath, weight management and metabolism (i.e., nutritional heath) Human health is promoted as indicated by biochemical markers including for example, blood sugar levels, lipid chemistry, liver function, full blood count, thyroid function, markers of inflammation (ESR and C-reactive protein), and stool classifications. In addition the compositions of the invention are further useful, when applied topically in promoting skin heath.

The term "prebiotic" as used herein includes compounds that stimulate the growth and or activity of bacteria.

The term "probiotic bacteria" or "probiotics" or "Microbiotic Composites™" as used herein, refers to microorganisms which when administered for nutritional intervention in adequate amounts confer a health benefit to the consumer. Heath benefit can be measured by any method known in the art, for example, as indicated by biochemical markers including for example, blood sugar levels, lipid chemistry, liver function, full blood count, thyroid function, markers of inflammation (ESR and C-reactive protein), and stool classifications.

The probiotics according to the invention may be viable or non-viable. In case the probiotics are non-viable, they have to be substantially structurally intact, meaning that these non-viable micro-organisms are still sufficiently intact to avoid or delay disintegration in the distal intestinal tract thereby enabling the interaction of (conserved structures of) the non-viable micro-organisms with the immune system, particularly the mucosal immune system. The non-viable probiotics are metabolically-active. By "metabolically-active" is meant that they exhibit at least some residual enzyme activity characteristic to that type of probiotic By the term "postbiotic" as used herein refer to the non-viable bacterial products or metabolic by products from the probiotic organism.

By the term "non-viable" as used herein is meant a population of bacteria that is not capable of replicating under any known conditions. However, it is to be understood that due to normal biological variations in a population, a small percentage of the population (i.e. 5% or less) may still be viable and thus capable of replication under suitable growing conditions in a population which is otherwise defined as non-viable.

By the term "viable bacteria" as used herein is meant a population of bacteria that is capable of replicating under suitable conditions under which replication is possible. A population of bacteria that does not fulfill the definition of "non-viable" (as given above) is considered to be "viable".

By the term "bioactive component" as used herein is meant a component which has a physiological effect upon the body when consumed in adequate amounts.

Unless stated otherwise, all percentages mentioned in this document are by weight based on the total weight of the composition.

Prebiotics used in the product according to the present invention may be any conventional prebiotic. The prebiotic is food grade. It is preferred that the prebiotic is inulin, fructo-oligosaccharides, or gluco-oligosaccharides.

The probiotic bacteria used in the product according to the present invention may be any conventional probiotic bacteria. The probiotic bacteria is GRAS (Generally Recognized As Safe). It is preferred that the probiotic bacteria are selected from the family Lactobacillacea and or *Bifidobacterium*.

Suitable types of probiotic bacteria which may be used include *Pediococcus acidilactici, Pediococcus pentosaceus, Lactobacillus plantarum* and *bifidobacterium animalis*.

In preferred compositions, the probiotic bacteria *Pediococcus acidilactici, Pedococcus pentosaceus* and *Lactobacillus plantarum* are present in equal proportions.

The levels of the probiotic bacteria to be used according the present invention will depend upon the types thereof. It is preferred that the present product contains probiotic bacteria in an amount between $10^5$ and $10^{11}$ colony forming units per gram.

In some embodiments of the invention, the probiotic bacteria employed are viable probiotic bacteria. The use of viable probiotic bacteria offers the advantage that these probiotic bacteria may become a part of the intestinal microflora, thereby providing additional health benefits.

The probiotic bacteria according to the invention may be produced using any standard fermentation process known in the art. For example, solid substrate or submerged liquid fermentation. The fermented cultures can be mixed cultures, Microbiotic Composites™ or single isolates. The probiotic bacteria are anaerobically fermented. The probiotic bacteria are a combination of solid substrate and a submerged liquid fermentation. In preferred compositions, the Lactobacillacea produced by solid substrate fermentation and submerged liquid fermentation are mixed in equal proportions.

In some embodiments the probiotic bacteria are anaerobically fermented in the presence of carbohydrates. Suitable carbohydrates include inulin, fructo-oligosaccharide, and gluco-oligosaccharides.

After fermentation the bacteria are harvested by any known methods in the art. For example the bacteria are harvested by filtration or centrifugation, or simply supplied as the ferment.

The bacteria are dried by any method known in the art. For example the bacteria are dried by liquid nitrogen followed by lyophilization.

The compositions according to the invention have been freeze dried to moisture content less than 20%, 15%, 10% 9%, 8%, 7%, 6%, 5%, 4%, 3%, 2%, or 1%. Preferably, the composition according to the invention has been freeze dried to moisture content less than 5%.

In some embodiments the freeze dried powder is ground to decrease the particle size. The bacteria are ground by conical grinding at a temperature less than 10° C., 9° C., 8° C., 7° C., 6° C., 5° C., 4° C., 3° C., 1° C., 0° C., or less. Preferably the temperature is less than 4° C.

For example the particle size is less than 1500, 1400, 1300, 1200, 1100, 1000, 900, 800, 700, 600, or 500 microns. Preferably, the freeze dried powder is ground to decrease the particle size such that the particle size is less than 800 microns. Most preferred are particle sizes less than about 400 microns. In most preferred embodiments the freeze dried powder has a mean particle size of 295 microns, with 60% of the mixture in the size range between 175-900 microns. In various embodiments the freeze dried powder is homogenized.

The postbiotic is produced by collecting the supernatants for each of the individual anaerobic fermentations and drying the mixture. Preferably the supernatants are combined prior to drying. The postbiotics are dried by any method known in the art. For example the postbiotics may be freeze dried.

The supernatants are freeze dried to moisture content less than 20%, 15%, 10% 9%, 8%, 7%, 6%, 5%, 4%, 3%, 2%, or 1%. Preferably, the composition according to the invention has been freeze dried to moisture content less than 5%.

The compositions of the present invention are formulated for oral administration including chewable foods, beverages, liquids, tablets, capsules, powders, and granulates. In a preferred embodiment the compositions have been formulated into a tablet. In another preferred embodiment the compositions have been formulated into a capsule. In yet another preferred embodiment the compositions have been formulated into granulated or water soluble powders. Further preferred compositions can be formulated into liquids, creams, lotions, gels dispersions or ointments for topical administration.

When formulated the composition may contain further ingredients, including ingredients that have a favorable impact on health, flavour, formulating or tableting. Non-limiting examples of additional ingredients that may suitably be incorporated in the present composition are: vitamins, minerals, nutritional supplements (e.g., fiber), fungal extracts, botanical extracts, sweeteners, flow aids, and fillers.

When formulated for oral administration the compositions comprise at least 0.1, 1, 5, 10, 15, 20, 25, 30, 35, 40, 45, 50, 55 or more w/w % of the pre-, pro- and post probiotic mixture.

In preferred embodiments the compositions of the invention are formulated in to a tablet and comprise minerals, vitamins, sugars, tableting aids and flavoring.

Minerals include for example Calcium Carbonate, Calcium Lactate, Calcium Chloride, Calcium Phosphate (dibasic), Sodium Chloride, Potassium Citrate monohydrate, Potassium sulfate, Potassium Phosphate monobasic, Magnesium Oxide, Manganese Carbonate, manganese glucanate, Ferric Citrate, Zinc Carbonate, Zinc glucanate, Cupric Carbonate, Potassium Iodate, Sodium Selenite pentahydrate, Chromium potassium sulfate dodecahydrate, Ammonium paramolybdate tetrahydrate, Sodium meta-silicate nonahydrate, Lithium chloride, boric acid, sodium fluoride, Nickel Carbonate hydroxide tetrahydrate, or ammonium meta-vanadate. Minerals are formulated at a concentration of about 0.1% to 10%, w/w, 0.1% to 5.0% w/w or any specific value within said range. In specific embodiments, minerals are formulated at a concentration of about 5% w/w, 4%, 3% w/w, 2% w/w, 1% w/w, 0.9% w/w, 0.8% w/w, 0.7% w/w, 0.6% w/w, 0.5% w/w, 0.4% w/w, 0.3% w/w, 0.2% w/w, 0.1% w/w or less.

Vitamins include for example, Vitamin B1, B2, B3, B5, B6, B7, B9, B12, Vitamin C, Vitamin D, Vitamin E, Vitamin A and/or K. Preferred are Vitamin B1, B3, B6 B12, Vitamin C, Vitamin D3, or Vitamin E acetate. Vitamins are formulated at a concentration of about 0.01% to 10%, w/w, 0.1% and 5 w/w %, or any specific value within said range. In particular vitamins are formulated at a concentration of about 5% w/w, 4%, 3% w/w, 2% w/w, 1% w/w, 0.9% w/w, 0.8% w/w, 0.7% w/w, 0.6% w/w, 0.5% w/w, 0.4% w/w, 0.3% w/w, 0.2% w/w, 0.1% w/w or less.

Sugars include for example, dextrose, sucrose, fructose, inulin, trehalose or salts of gluconic acid. Preferred sugars include dextrose, fructose, inulin, fructo-oligosaccharides, gluco-oligosaccharides, galcto-oligosaccchari des, substituted mannans, such as ace mannan and galcto mannans, or Sucralose. Sugars are formulated at a concentration of about 10% to 50%, w/w, 20%-40% w/w, or any specific value within said range. In particular vitamins are formulated at a concentration of about 50% w/w, 45% w/w, 40%, 35% w/w, 30% w/w, 25% w/w, 20% w/w, 15% w/w, 10% w/w, or less.

Tableting aids include for example, carboxylic acids such as malic, maleic, citric, iso-citric and succinic, and salts thereof, $SiO_2$, *Aloe* Vera, saturated and unsaturated linear and branched fatty acids and their salts, or fatty alcohols. Preferred tableting aides are malic acid, citric acid, stearic acid or Magnesium stearate. Tableting aides are formulated at a concentration of about 1% to 10%, w/w, 2.5% and 7.5 w/w % or any specific value within said range. In particular vitamins are formulated at a concentration of about 10% w/w, 7.5%, 5% w/w, 4%, 3% w/w, 2% w/w, 1% w/w, or less.

Any natural or artificial food grade flavorings maybe used including Banana, Cinnamon, Grape, Orange, Citrus, Peach, Pear, Pineapple, Apple, Berry, Coconut, Chocolate, Vanilla, Strawberry, Wintergreen, Spearmint, Peppermint or Ginger. Preferred flavorings are ginger or natural berry flavorings. Flavorings are formulated at a concentration of about 0.1% to 10%, w/w, 0.5% and 5 w/w % or any specific value within said range. In particular flavoring agents are formulated at a concentration of about 5% w/w, 4%, 3% w/w, 2% w/w, 1% w/w, 0.9% w/w, 0.8% w/w, 0.7% w/w, 0.6% w/w, 0.5% w/w, 0.4% w/w, 0.3% w/w, 0.2% w/w, 0.1% w/w or less.

In a particularly preferred embodiment the probiotic compositions of the invention are formulated into a tablet and comprise 58.0% w/w pre-, pro- and post probiotic mixture; 0.58% w/w calcium lactate, 2.95% w/w vitamins, 2.11% w/w minerals, 31.70% w/w sugars, 2.66% w/w tableting aids and 2.00% flavoring.

In yet another preferred embodiment the compositions of the invention are formulated in to a capsule and comprise fungal extracts, botanicals, vitamins, minerals, fiber and fillers. Fungal extracts may include whole components or specific extracts from: *Gandoderma lucidium, Lentinus edodes, Hericium erinaceous, Agaricus blazei, Cordyceps sinensis, Grifola frondosa, Coriolus veriscolor, Coprinus comatus*, or *Grifola frondosa*.

Botanicals may include: *Rhodiola Rosea* extract, *Aloe Barbedensis, Yucca Schidigera, Aloe vera, Boswellia* extract, *Acacia Catechu, Scutellaria baicalensis, moringa* or turmeric.

Fillers may include inulin, Fructo-oligosaccharides, gluco-oligosaccharides, rice flour, [rice bran, tapioca] silicon dioxide, stearic acid, or Magnesium stearate, and galactose.

In yet another preferred embodiment the compositions of the invention are formulated into a capsule containing only the Microbiotic Composites™ in concentrations ranging from 5-500 mg delivering $10^5$-$10^{11}$ cfu/g, and preferably $10^6$-$10^{10}$ cfu/g.

The compositions of the present invention may include additional nutritional supplements such as Glucosamine HCL or Chondroitin Sulfate. They may also include materials for relief of chronic pain and inflammation such as methylsulfonylmethane.

The compositions of the invention are useful in methods of treating various disorders and signs and symptoms thereof. Specifically the compositions are used to promote digestive health, metabolism (nutritional heath) and weight management when administered orally. For example, the composition are used to treat or alleviate a sign or symptom a digestive disorder such as of constipation (e.g. irritable bowel syndrome with constipation (IBS-C) or chronic idiopathic constipation (CIC), diarrhea (e.g. chronic diarrhea), dysbiosis, Crohn's disease, food allergy, lactose intolerance and chronic gastrointestinal inflammatory diseases such as pouchitis and ulcerative colitis. The compositions are also used to reduce morbidities associated with metabolic syndrome X.

In addition, the composition of the invention are used to promote skin heath and wound healing when administered topically. For example, the compositions are used to treat or alleviate a sign or symptom of skin disorders such as for example rosacea, acne, dermatitis, eczema and psoriasis.

Unless stated otherwise, all percentages mentioned in this document are by weight based on the total weight of the composition.

A better understanding of the present invention may be given with the following examples which are set forth to illustrate, but are not to be construed to limit the present invention.

EXAMPLES

Example 1: Preparation of the Microbiotic Composition

The Microbiotic Composite™ composition of the present invention is prepared via a combination of submerged liquid fermentations and solid substrate fermentations.

Premix A: Solid Substrate Fermentation of *Lactobacillus*:

Individual purified isolates of *Pediococcus acidilactici*, *Pediococcus pentosaceus* and *Lactobacillus plantarum* were grown-up in separate fermenters using standard anaerobic submerged liquid fermentation protocols. The individual organisms were recovered from the fermenters via centrifugation, mixed together in equal proportions on a weight basis, then added to the following mixture: 1 part inulin, 2.2 parts isolated soy protein, 8 parts rice flour with 0.25% w/w sodium chloride, 0.045% w/w Calcium carbonate, 0.025% w/w Magnesium sulphate, 0.025% w/w Sodium phosphate, 0.012% w/w Ferrous sulphate and 29.6% water. This mixture was allowed to ferment for up to 5 days at 30° C. Upon completion of the fermentation, the entire mixture was freeze dried to a moisture content less than 5%, ground to an average particle size of 295 microns, with 60% of the product in the size range between 175-840 microns, and homogenized. The final microbial concentration of the powdered product is between $10^9$ and $10^{11}$ CFU/g.

Premix B: Submerged Fermentation of *Lactobacillus*:

Individual, purified isolates of *Pediococcus acidilactici*, *Pediococcus pentosaceus*, and *Lactobacillus plantarum* were grown-up in separate fermenters in the presence of Inulin using standard anaerobic submerged liquid fermentation protocols. After fermentation the individual cultures were filtered, centrifuged, freeze dried to a moisture level less than about 5%, then ground to a mean particle size of 295 microns, with 60% of the product in the size range between 175-840 microns, and homogenized. The final microbial concentration of the powdered product is between $10^9$ and $10^{11}$ CFU/g.

Premix C: Fermentation Supernatant:

The supernatants remaining after centrifugation of the organisms produced from the submerged fermentations of Premix B above were collected, mixed together, freeze dried to a moisture level less than about 5%, then ground to a mean particle size of 295 microns, with 60% of the product in the size range between 175-840 microns, and homogenized.

A final composition is prepared by combining premixes A, B, and C in equal weights and mixing this composition to homogeneity.

Example 2: Formulation of Dosages for Clinical Studies

The final compositions from Example 1 were formulated into tablets, capsules, and powders for human clinical studies according to the following compositions:

| | Formulation | | | | |
|---|---|---|---|---|---|
| | A | B | C | D | E |
| | FORM | | | | |
| Ingredient | Tablet % w/w | Capsule % w/w | Capsule % w/w | Powder % w/w | Capsule % w/w |
| Composition of Example 1 | 58.0% | 3.78% | 50.23% | 1.36% | |
| Composition of Example 1 using Premix B and C only | | | | | 100% |
| Minerals | 0.58% | 2.77% | 0.80% | 0.10% | |
| Vitamins | 2.9% | 27.02% | 0.03% | 3.50% | |
| Sugars | 32.0% | 1.19% | — | 5.80% | |
| Tableting Aids | 4.42% | — | — | | |
| Flavoring | 2.1% | — | — | 3.00% | |
| Fungal Extracts | — | 36.40% | 28.05% | | |
| Botanical Extracts | — | 10.14% | — | 10.90% | |
| Methylsulfonyl-methane | — | — | — | 29.21% | |
| Glucosamine HCL | — | — | — | 29.21% | |
| Chondroitin Sulfate | — | — | — | 14.60% | |
| Fillers | — | 4.55% | 2.19% | 2.53% | |
| Capsule | — | 14.15% | 18.70% | — | |

Final Characteristics of the tablets from Composition A are:

| | |
|---|---|
| Appearance | Off white to medium brown |
| Dimensions | 0.555 × 0.555 in² |
| Avg. Tablet Wt. | 1.2 grams |
| Hardness | 32-38 kp |
| Friability | <=2% loss |

Example 3: Effect of Claimed Composition on Nutritional Health

Overview:

A small base-control study comprising 30 male and female patients aged between 18 and 53 classified as obese with signs of metabolic syndrome.

Patients were screened based by a medical practitioner for overall health and Body Mass Index (BMI).

Design:

The participants were given 500 mg/day (two 250 mg capsules) of a product containing the Microbiotic Composite™ of Example 2E.

The participants were otherwise advised not to make changes to their normal diet of level of physical activity or exercise.

Following three months of usage, the panelists were interviewed to determine their overall perception of the products benefits. In addition clinical testing was conducted on the subjects pre and post trial. This included:

Changes in weight (body mass index (BMI), body fat, waist and hip)

Blood metabolism profiles (blood glucose and dyslipidemia)

Liver Function

Changes in bowel habits and stool consistency (Based on Bristol Stool Charts)

Materials:

A Microbiotic Composite™ was formulated in 250 mg size capsules according to the composition in Example 2E.

Figure 2:
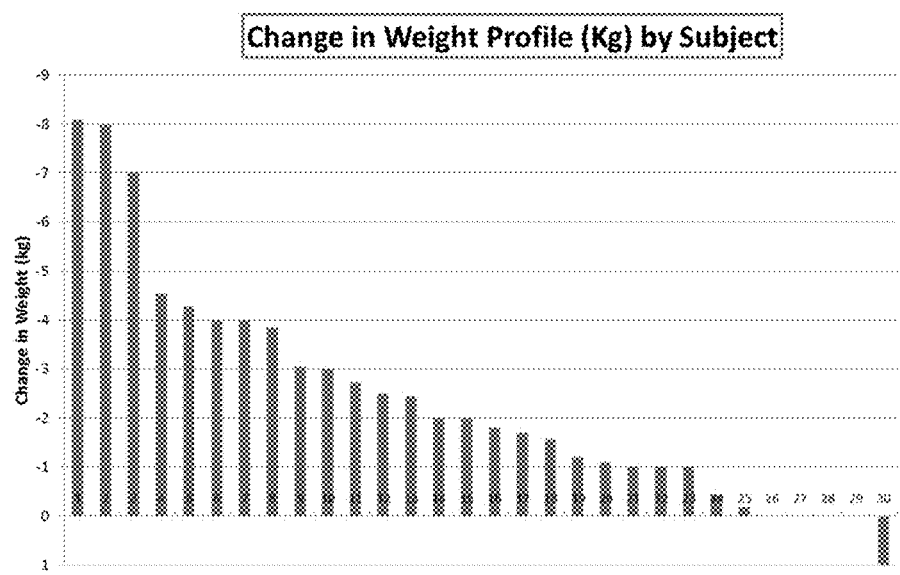
FIG. 2: Change in weight profile by subject following 12 week ingestion of Microbiotic Composite Example 2E
Figure 3:
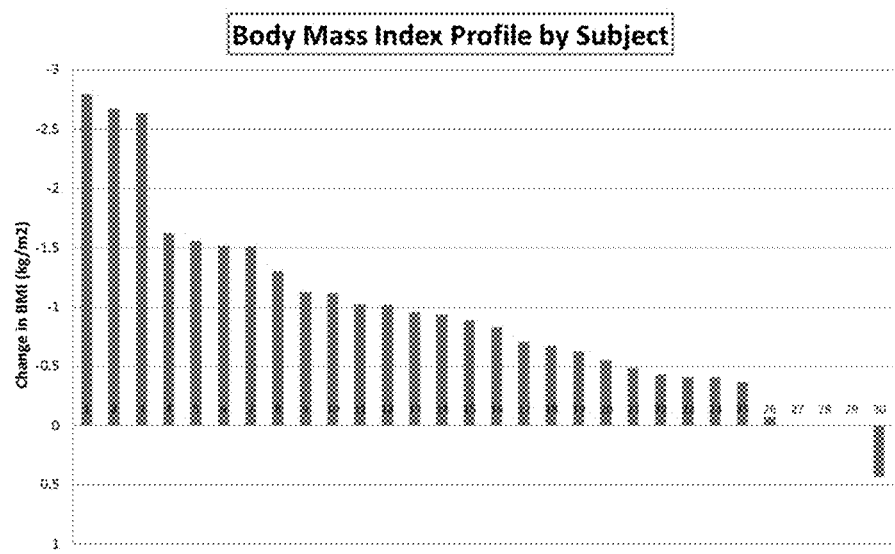
FIG. 3: Body mass index profile by subject following 12 week ingestion of Microbiotic Composite Example 2E.

Results:

A) Weight Loss:

Overall, there was a significant effect on both weight loss and/or waist reduction following 12 weeks of ingestion of the product. Subjects lost and average of 2.4 kg over 12 weeks of the test (FIGS. 1, 2, and 3).

Key Learning

There was total of 27 participants in this group. 12 subjects showed both a weight reduction, as well as a reduction in waist measurement. The remainder showed weight loss only.

Grouping both together it takes into account conversion of peripheral fat to muscle in this contexts Two participants remained neutral in both weight as well as waist measurement. One participant gained weight.

Figure 4:
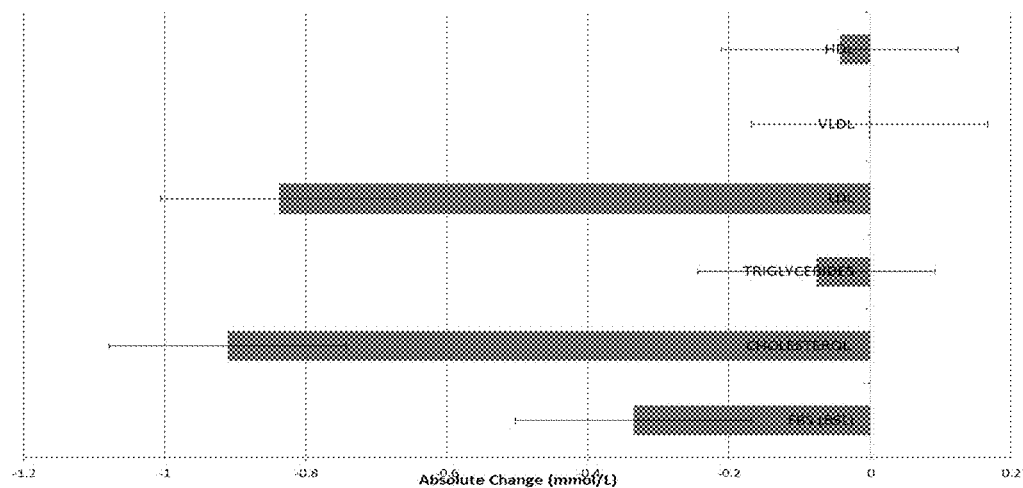
FIG. 4: Composite Blood sugar (FBS), Cholesterol (LDL, VLDL, HDL) and Triglyceride levels following 12 week ingestion of Microbiotic Composite Example 2E.

B) Results in Blood Marker Levels:

Significant reductions were observed among subjects in blood sugar (FBS), cholesterol and LDL (FIG. 4).

Figure 5:
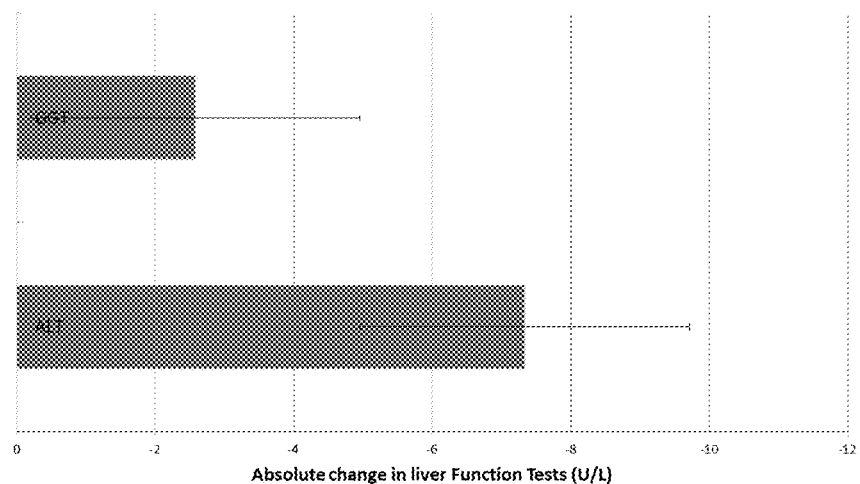
FIG. 5: Composite Lever enzyme (ALT and GGT) levels following 12 week ingestion of Microbiotic Composite Example 2E.
Figure 6:
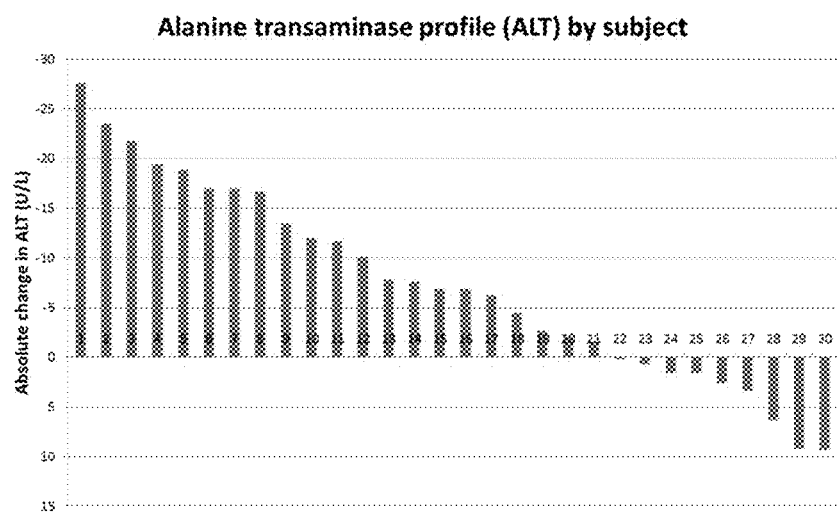
FIG. 6: Alanine transaminate level by subject following 12 week ingestion of Microbiotic Composite Example 2E.

C) Liver Function Results:

Significant reductions were also observed in the liver enzymes ALT and GGT which are correlated with reduced liver stress (FIGS. 5 and 6).

Hepatic Enzyme Markers ALT/GGT: Alanine aminotransferase (ALT) and γ-glutamyltransferase (GGT) are strongly associated with obesity, insulin resistance, and metabolic syndrome. Research has associated the risk of type 2 diabetes to be significantly higher with increasing levels of ALT and GGT, particularly in men.

D) Digestive Health Results:

Significant improvements were observed in the bowel habits of 100% of test subjects.

Improvements were seen in constipation or loose bowels, and in stool consistency; as measured by subjects using an industry standard tool, the Bristol Stool Chart (BSC). Bristol stool chart levels of 1 or 2 are typically representative of dysbiosis in most Western countries, whereas looser stools in values of 5-7 are quite common in most developing countries.

The overall results show a normalization of bowel habits with a predominant shift to level 3-4 noted with improved stool consistency.

Figure 7:
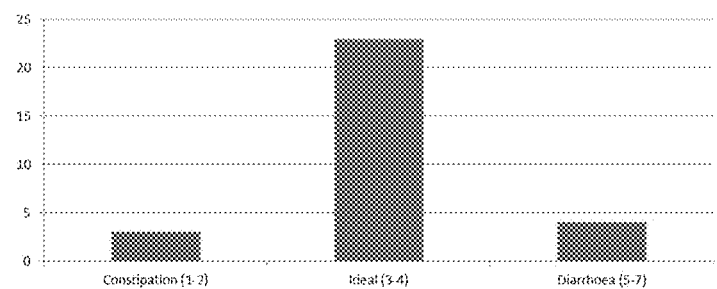
FIG. 7: Bowel behavior of subjects prior to ingestion of Microbiotic Composite Example 2E.
Figure 8:
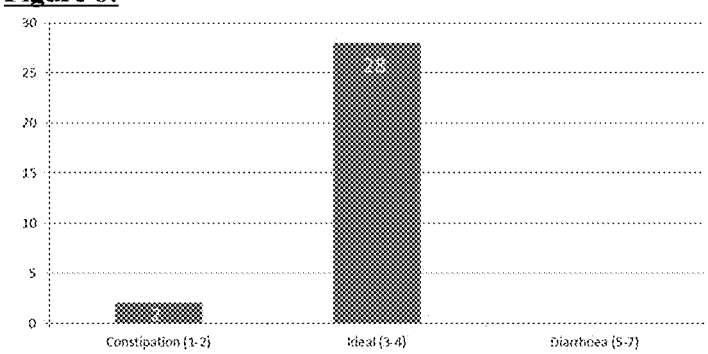
FIG. 8: Bowel behavior of subjects post ingestion of Microbiotic Composite Example 2E.
Figure 9:
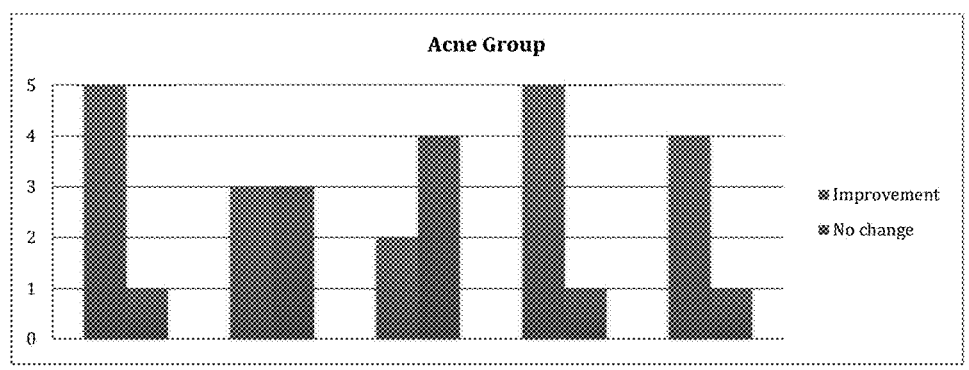
FIG. 9: Incidence of Acne during use of topical skin treatment comprising the Microbiotic Composite of Example 2E.
Figure 10:
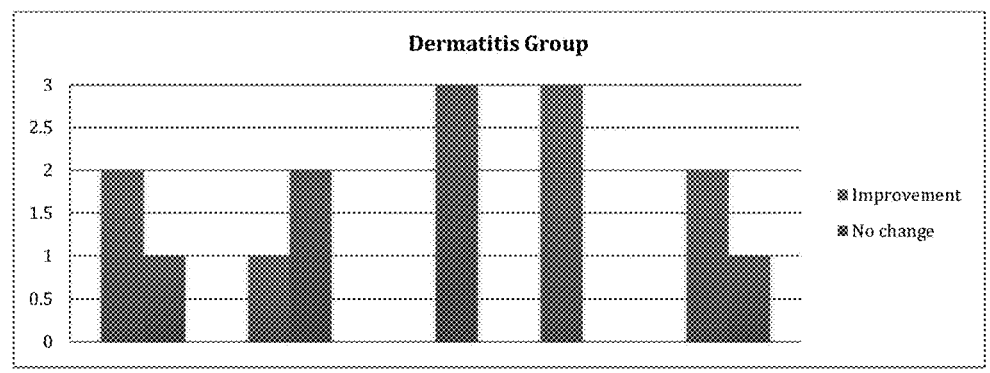
FIG. 10: Incidence of Dermatitis during use of topical skin treatment comprising the Microbiotic Composite of Example 2E.
Figure 11:
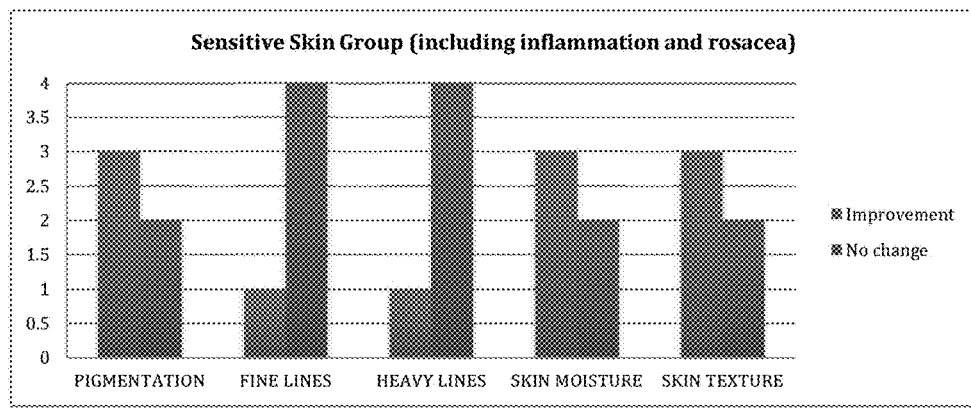
FIG. 11: Incidence of skin sensitivity during use of topical skin treatment comprising the Microbiotic Composite of Example 2E.
Figure 12:
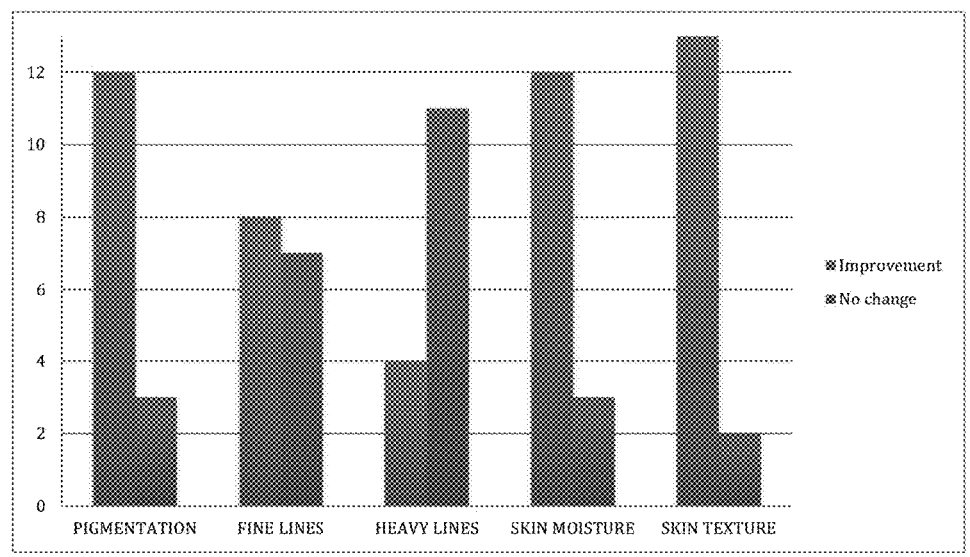
FIG. 12: Number of panelists responding to questionnaire regarding skin condition during use of topical skin treatment comprising the Microbiotic Composite of Example 2E.
Figure 13:
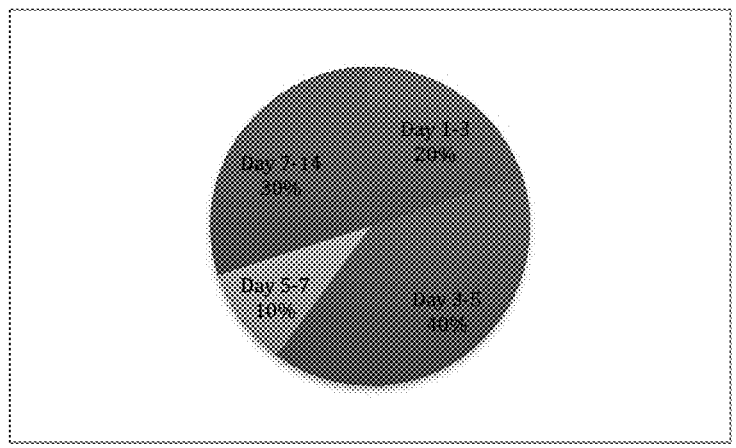
FIG. 13: Time to clinical improvement in skin health when using a topical skin treatment comprising the Microbiotic Composite of Example 2E.

FIG. 7: Pre-Clinical:

3—people reported constipation and had separate hard lumps to sausage shaped but lumpy 23—people were in a normal range with sausage, with surface cracks to sausage, smooth and soft 4—people reported soft, fluffy, or watery consistency FIG. 8: Post-Clinical:

100% of people had improved bowel function

2—people had slight changes in consistency

1—person improved their stool consistency from separate hard lumps to an ideal stool consistency 23—people were in a normal range but improved their stool consistency 4—people improved from soft, fluffy, or watery to an ideal stool consistency Example 4: Facial and Body Skin Care Study Effects on Various Skin Types—A Case Control Study.

Overview

A topical probiotic formulation comprising the Microbiotic Composite™ of Example 2E was trialed in a variety of skin conditions including acne, dermatitis, eczema as well as sensitive skin types that included inflammation and rosacea. The beneficial effects documented included improvements in skin pigmentation, moisture, and texture, as well as pigmentation in various subgroups of the study. For example, in the eczema subgroup there was a significant improvement in pigmentation, moisture and texture. This result was also noted in the acne and dermatitis subgroups. The formulation demonstrated clinical effects with the majority of responses within the first five days of using the products in the study (60%). This was also reflected in an overall trend demonstrating that 75% of patients reported some improvements.

Design

The study was designed as a case-control study looking for improvement in skin conditions such as acne, dermatitis, eczema, and generalized information on sensitive skin and rosacea.

Protocol and Materials:

A total of 25 subjects were recruited for the study from a skin care clinic based in Sydney, Australia. The participants in the study were regular clientele who all exhibited some form of skin condition that had been non-amendable to traditional prior treatments using their current skin care regime.

All participants were reviewed by a medical practitioner prior to commencement of the study.

Subjects were advised to use two skin care products, a Deep Moisturizer Cream and a Topical Gel, for both facial and body application. Both products were to be used as subjects would normally apply such products to problematic skin areas, but were instructed to use the products at least once daily for four weeks.

The Deep Moisturizer Cream was composed of the following materials:

65% Water
2% Caprylic/Capric Triglyceride
2% Propanediol
2% Aluminum Starch Octenylsuccinate
3% Microbial Composite™ (Example 2E Composition)
2% Saccharide Isomerate
2% Stearic Acid
2% Potassium Cetyl Phosphate (The following ingredients totaled to 20% of the formula by weight and were added in amounts of less than 1% each)

Disodium EDTA, Hydrogenated Palm Glycerides, Butyrospermum Parkii (Shea) Butter, Sodium Hydroxide, Ammonium Acryloyldimethyltaurate/VP Copolymer, Hibiscus *Abelmoschus* Seed Extract, Butylene Glycol, Xanthan Gum, Glycerin, Carbomer, Polysorbate 20, Palmitoyl Oligopeptide, Palmitoyl Tetrapeptide-7, *Citrus Aurantium Dulcis* (Orange) Fruit Extract, *Citrus Aurantium Dulcis* (Orange) Peel Extract, *Lavandula Angustifolia* (Lavender) Flower/Leaf/Stem Extract, *Elettaria Cardamomum* Seed Extract, *Gardenia Tahitensis* Flower Extract, *Pyrus Malus* (Apple) Fruit Extract, *Prunus Armeniaca* (Apricot) Fruit Extract, *Hibiscus Abelmoschus* Extract, *Eugenia Caryophyllus* Clove Flower Extract, *Jasminum Officinale* (Jasmine) Flower/Leaf Extract, *Vanilla Planifolia* Fruit Extract, *Polianthes Tuberosa* Extract, *Hedychium Spicatum* Extract, *Plumeria Ruba* Flower Extract, Phenoxyethanol, Caprylyl Glycol, Ethylhexylglycerin, Hexylene Glycol The Topical Gel was composed of the following materials:

65% Water
5% Glycerin
3% Microbial Composite™ (Example 2E Composition)
3% Polysorbate 20

(The following ingredients totaled to 24% and were added in amounts of less than 1 percent each)

Disodium EDTA, Allantoin, Xanthan Gum, Phenoxyethanol, Caprylyl Glycol, Ethylhexylglycerin, Hexylene Glycol, Ammonium Acryloyldimethyltaurate/VP Copolymer, Caprylic/Capric Triglyceride, *Citrus Aurantium Dulcis* (Orange) Fruit Extract, *Citrus Aurantium Dulcis* (Orange) Peel Extract, *Lavandula Angustifolia* (Lavender) Flower/Leaf/Stem Extract, *Elettaria Cardamomum* Seed Extract, *Gardenia Tahitensis* Flower Extract, *Pyrus Malus* (Apple) Fruit Extract, *Prunus Armeniaca* (Apricot) Fruit Extract, *Hibiscus Abelmoschus* Extract, *Eugenia Caryophyllus* (Clove) Flower Extract, *Jasminum Officinale* (Jasmine) Flower/Leaf Extract, *Vanilla Planifolia* Fruit Extract, *Polianthes Tuberosa* Extract, *Hedychium Spicatum* Extract, *Plumeria Ruba* Flower Extract, Sodium Hydroxide The exclusion criteria for the study were based on previous exposure to systemic vitamin A therapies. In addition, participants were asked to stop using any other topical therapies on their faces for the month of the study. Clients were advised to refrain from using ablative technologies (including microdermabrasion and skin needling), light based therapies (including IPL and laser) or chemical peels (such as lactic acid, TCA or Jessner's) for the duration of the study.

Data was collected via means of a questionnaire, photographs at baseline and at the completion of the study. Over the duration of the test, participants were evaluated weekly via telephone interviews.

Data included subjective questionnaire parameters around skin improvement. Objective parameters included an assessment of skin pigmentation, fine line and heavy line reduction, overall skin moisturizing, as well as skin texture. Adverse events were monitored either via direct observation, or subjective assessment of erythema, or pain on using the product based on participant responses. A medical practitioner reviewed all adverse events.

Results:

15 participants completed the full study requirements.

In the acne subgroup, beneficial effects were noted on skin pigmentation, skin moisture as well as skin texture (N=6). In fact, N=5 persons reported improvement in skin moisture and N=4 on skin texture on completion of the study. Further, an overwhelming N=5 reported benefits in pigmentation. As is noted in all subgroups (discussed below), there were subtle improvements in fine lines and heavy lines. However, most participants reported no or minimal changes. In the dermatitis subgroup (N=3), similar results were noted. There is a significant improvement in skin moisture (N=3) and modest improvement in skin texture and skin pigmentation (N=2) on using the product. In the eczema subgroup (N=6), there was a significant improvement in pigmentation, moisture and texture when using the product (N=5, 5 and 6 respectively). Results on sensitive skin (including inflammation and rosacea) were not significant, although there was an overall trend favoring noted in skin moisture, skin texture and pigmentation. The results are not as apparent as those noted in other skin conditions. The results described are noted in the figure below.

The results on skin pigmentation, skin moisture and skin texture can be best appreciated when incorporating all the data together. As is noted in FIG. 2 below, a total of 12 participants reported an improvement in skin pigmentation as compared to 3 who showed no change. A similar result was also noted on skin moisture. The results were better when looking at skin texture with a total of 13 participants showing improvement, with two showing no change. The results on fine and heavy lines were not significant.

A further interesting aspect noted in the study was the time to observe a clinical response. Most topical agents can vary from several days to several months. In fact, rapid responses are typically only noted for corticosteroid preparations.

However, in this particular study, the time to clinical response was quite fast. For example, within the first 72 hours, 20% of the participants reported a time to clinical response. A further 40% showed improvement in skin quality by day five of the study. A further 10% had some changes by day seven. By two weeks, a further 30% had shown a physiological change to their skin. Overall, 100% of all participants who completed the study had a clinical response within two weeks. This result is summarized in the pie chart below.

Figure 14:
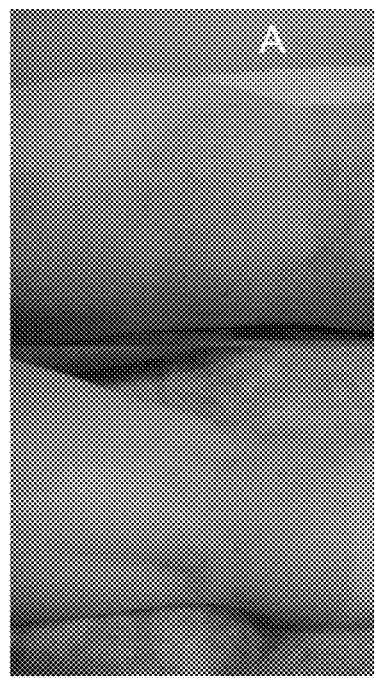
FIG. 14: Photographic images depicting the effect of the topical probiotic agent on eczema on the leg. The panel on the left (panel A) shows photographs taken from the posterior aspect of the leg. The image above was taken prior to application of the product whilst the image below it was taken at the completion of the study. Similarly, a photograph taken of the medial aspect of the same patient's leg shows a similar improvement (panel B).
Figure 14:
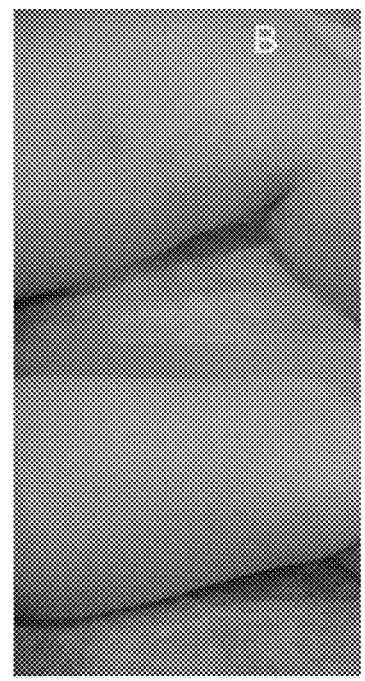

The most striking feature noted on using this topical agent is the improvement on specific skin conditions. For example, FIG. 14 shows the effect of the topical agent on a patient who had eczema on her leg. The panel on the left which shows the posterior view of the leg, shows significant resolution off the erythema associated with eczema based on the before (top) and after (bottom) views. A similar effect was noted on the lateral aspect of the leg shown on the right of the same image.

Figure 15:
FIG. 15: Photographic images depicting the effect of the topical probiotic agent on a combination skin (acne and dermatitis). The image to the left is one of the patients taken prior to application of topical agent. Image to the right was taken following the completion of the study.

These effects were not only noted on eczema. For example, FIG. 15 shows photographic images of a patient who had a combination of acne and dermatitis on her face. The image shown on the left shows significant dermatitis on the malar aspect the face as well as the tear troughs prior to treatment (left), and resolution thereof (right). In addition, the cystic acne noted on the chin significantly improved at the completion of the study, and is noted on the figure on the right.

Figure 16:
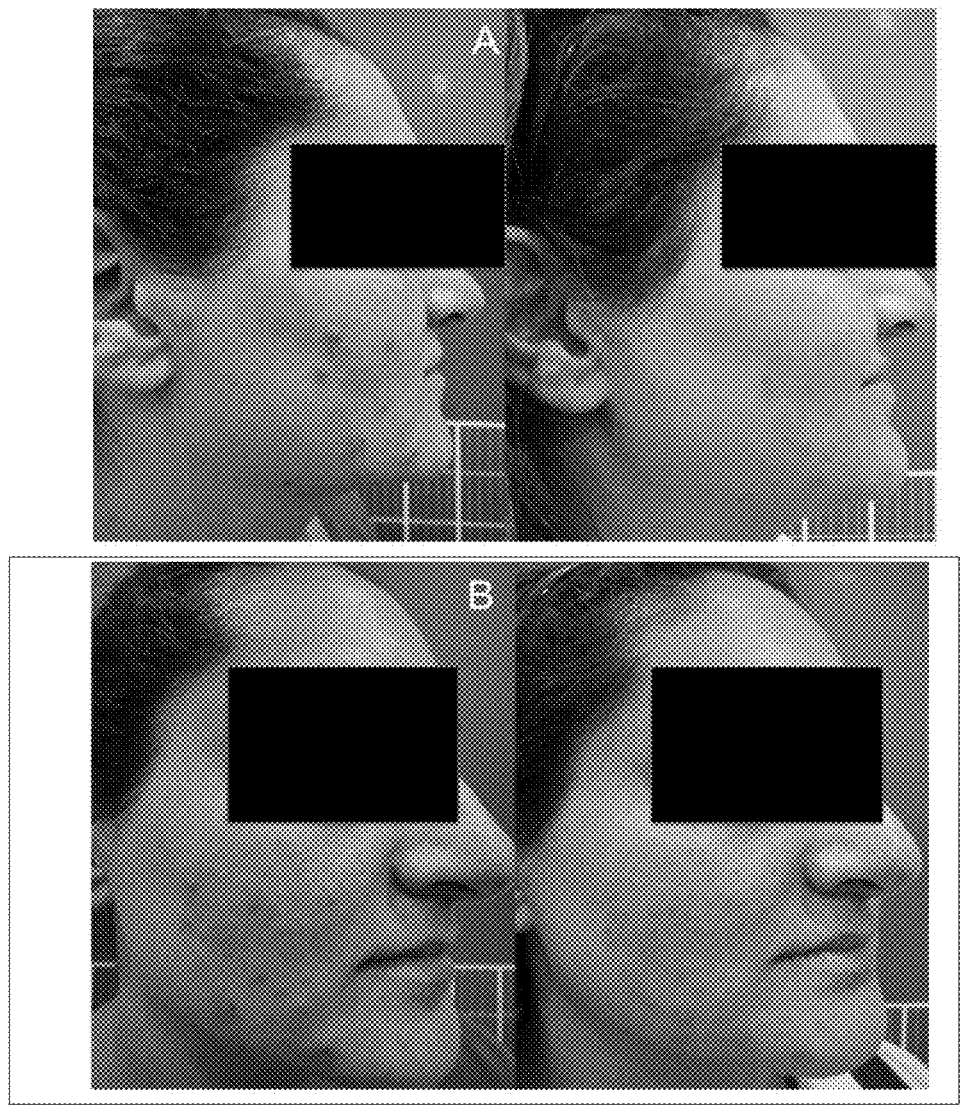
FIG. 16: Photographic images of a patient with acne pre and post application of the topical probiotic. The images shown to the left depict the extent of the disease prior to commencement of therapy. The images on the right show a resolution of the inflammatory changes associated with acne following completion of study. Panel A (lateral views), Panel B (oblique views).

A similar effect was noted on cystic acne. FIG. 16 shows images of acne before (left) and after (right) application of the topical probiotic agent. As is noted in the figure, significant changes are noted when viewing the skin from a lateral aspect (panel A above) as well as oblique aspects (panel B below).

Note: The figures shown were chosen to be representative of improvements in skin condition noted by most of the participants of the study.

CONCLUSION

Overall, panelists benefited from using the product for a variety of skin conditions including acne, dermatitis, eczema, as well as sensitive skin. Most participants reported an improvement in pigmentation, skin moisture, as well as skin texture. Results on fine and heavy lines were not significant. It is, however, important to note that this trial preparation did not include various topical excipients, such as vitamin A, vitamin B, vitamin C, alphahydroxy acids, idebenone. These agents have been shown to have beneficial effects on skin growths and often termed cosmeceuticals. It is contemplated that future iterations of this technology will contain such excipients with a view of improving overall physiological benefits.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A composition comprising:
   a. inulin,
   b. a probiotic comprising a mixture of *Pediococcus acidilactici*, *Pediococcus pentosaceus*, and *Lactobacillus plantarum* microorganisms produced by submerged liquid fermentation,
   c. a postbiotic derived from the liquid fermentation medium of the *Pediococcus acidilactici*, *Pediococcus pentosaceus*, and *Lactobacillus plantarum* microorganisms, wherein the postbiotic is prepared by:
      i. collecting the supernatants from the centrifugation of each of the individual anaerobic fermentations of the *Pediococcus acidilactici*, *Pediococcus pentosaceus*, and *Lactobacillus plantarum* organisms;
      ii. mixing the supernatants together;
      iii. freeze-drying the mixed supernatants to a moisture content less than about 5% by weight and
      iv. grinding the dried supernatants of step (iii) to a mean particle size of 295 microns, with 60% of the mixture in the size range between 175-900 microns,
   d. moringa,
   e. Boswellia extract, and
   f. fiber.

2. A method of improving human health in a subject, the method comprising orally administering to the subject the composition of claim 1.

3. The composition of claim 1, comprising at least 1% of inulin by weight.

4. The composition of claim 1, comprising at least 1% of the probiotic by weight.

5. The composition of claim 1, comprising at least 1% of the postbiotic by weight.

6. The composition of claim 1, formulated into a chewable food, skin cream, lotion, gel, or ointment.

7. The composition of claim 1, wherein the concentration of the *Pediococcus acidilactici*, *Pediococcus pentosaceus*, and *Lactobacillus plantarum* microorganisms is between $10^9$ and $10^{11}$ CFU per gram of the mixture.

8. The method of claim 2, wherein the composition is administered as a tablet, capsule, powder, or granulate.

9. The method of claim 8, wherein the tablet, capsule, powder or granulate contains between about 5-800 milligrams of the composition.

10. A method for treating a digestive disorder in a subject, the method comprising orally administering to the subject the composition of claim 1.

11. The method of claim 10, wherein the digestive disorder is constipation, diarrhea dysbiosis, Crohn's disease, food allergy, lactose intolerance pouchitis, or ulcerative colitis.

12. A method for reducing comorbidities associated with Metabolic Syndrome X in a subject, the method comprising orally administering to the subject the composition of claim 1.

13. A method for treating a skin disorder in a subject, the method comprising topically administering to the subject the composition of claim 6.

14. The method of claim 13, wherein the skin disorder is rosacea, acne, psoriasis, eczema, or dermatitis.

15. A method for improving wound healing in a subject having a wound, the method comprising administering to the wound the composition of claim 6.

* * * * *